(12) United States Patent
Frank

(10) Patent No.: US 12,203,910 B2
(45) Date of Patent: Jan. 21, 2025

(54) GAS MEASURING APPARATUS WITH A COMPACT DESIGN

(71) Applicant: Opus Inspection, Inc., East Granby, CT (US)

(72) Inventor: Holger Frank, Titisee-Neustadt (DE)

(73) Assignee: Opus Inspection, Inc., East Granby, CT (US)

( * ) Notice: Subject to any disclaimer, the term of this patent is extended or adjusted under 35 U.S.C. 154(b) by 169 days.

(21) Appl. No.: 17/961,633

(22) Filed: Oct. 7, 2022

(65) Prior Publication Data

US 2023/0133140 A1    May 4, 2023

Related U.S. Application Data

(63) Continuation of application No. PCT/EP2021/053829, filed on Feb. 17, 2021.

(30) Foreign Application Priority Data

Apr. 8, 2020   (DE) .......................... 102020109887.1

(51) Int. Cl.
    *G01N 33/00*    (2006.01)
(52) U.S. Cl.
    CPC ..... *G01N 33/0009* (2013.01); *G01N 33/0018* (2013.01)

(58) Field of Classification Search
    CPC ...................... G01N 33/0009; G01N 33/0018
    See application file for complete search history.

(56) References Cited

U.S. PATENT DOCUMENTS

| 6,606,897 | B1* | 8/2003 | Koyano | G01N 33/0009 |
| | | | | 73/431 |
| 9,360,467 | B1* | 6/2016 | Van Orsdol | G01N 33/225 |
| 2008/0190174 | A1* | 8/2008 | Kooi | G01N 33/006 |
| | | | | 73/31.01 |
| 2014/0309947 | A1 | 10/2014 | Gryska | |

FOREIGN PATENT DOCUMENTS

WO    WO-2017199404 A1 *  11/2017  ............... G01N 1/22

OTHER PUBLICATIONS

English translation of WO2017199404 accessed from worldwide.espacenet.com.*

* cited by examiner

*Primary Examiner* — Kristina M Deherrera
*Assistant Examiner* — Jean F Morello
(74) *Attorney, Agent, or Firm* — Von Rohrscheidt Patents

(57) ABSTRACT

A gas measuring apparatus including at least one measuring channel including at least one sensor unit; and a core body including a first part and a second part, wherein the first part is joined at the second part at a flat or planar interface, and wherein the at least one measuring channel is configured in the flat or planar interface.

10 Claims, 3 Drawing Sheets

GAS MEASURING APPARATUS WITH A COMPACT DESIGN

This application is a continuation of International application PCT/EP2021/053829 filed on Feb. 17, 2021, that claims priority from German patent application DE 10 2020 109 887.1 filed on Apr. 8, 2020. Both of which are incorporated in their entirety by this reference.

FIELD OF THE INVENTION

The invention relates to gas measuring apparatus including at least one measuring channel and at least one sensor unit arranged in the measuring channel.

BACKGROUND OF THE INVENTION

Gas measuring apparatuses are used e.g. to analyze exhaust gases or fuel gasses with respect to particular substances or aerosols or particles. Thus, typically all components in the gas measuring apparatus are connected by hoses. The hoses, however, can kink or can be squeezed which cuts off flow. In particular when the gas measuring apparatus is complex the hoses can be connected incorrectly or can disengage from a connection. This can make exhaust gas analysis more difficult.

Softeners can be released from the hose material so that the hose material becomes brittle and leaky. Cross sections of the hoses at transitions have different sizes which causes different flow velocities and turbulence. This can distort results of the analysis and make the exhaust gas analysis more difficult.

Known gas measurement apparatuses typically use venous materials. A component arrangement in the gas measuring apparatus where the components are connected by hoses typically requires a large amount of installation space so that a space saving component arrangement becomes more difficult which causes excessively high production costs.

BRIEF SUMMARY OF THE INVENTION

Therefore, it is an object of the instant invention to provide a gas measuring apparatus with a simple and compact configuration.

The object is achieved by a gas measuring apparatus including at least one measuring channel including at least one sensor unit; and a core body including a first part and a second part, wherein the first part is joined at the second part at a flat or planar interface, and wherein the at least one measuring channel is configured in the flat or planar interface.

Advantageously a gas path is implemented through the core body and not through a hose connection. Thus, an arrangement of various components in the core body can be achieved in a simple manner without a hose connection. This facilitates a compact functionality. Advantageously a kinking of hoses and a disengagement of the hoses from a hose connection is rendered impossible since there are no hoses. According to the invention installation space is minimized due to a compact and space saving configuration which helps to reduce productions costs.

Advantageously the interface is configured flat so that the at least one measuring channel can be sealed tight in a simple manner. Alternatively or additionally the joint can be configured planar so that the first part is separated from the second part by a simple separation plane. Thus a simple separation plane can be defined that separates the first part from the second part.

According to an advantageous embodiment of the invention at least one channel of a dilution flow is arranged in the core body. Thus the gas to be measured can be diluted and adapted to a sensitivity of the sensor.

According to an advantageous embodiment of the invention the second part of the base element is configured as a cover. The first part and the second part of the base element are advantageously bonded together. The invention advantageously uses a compact configuration which bonds the components into the gas measuring apparatus. Thus, the components remain in position even after vibrations and jolts.

According to an advantageous embodiment of the invention the bonded connection of the interface is formed by laser welding. Alternatively the bonded connection can be provided by another welding method. This has the advantage to no additional hose connections have to be plugged together or assembled. This helps to avoid fabrication errors. In particular one of the two parts of the base body can be configured transparent. Alternatively or additionally the other part of the base body can be configured non light permeable.

According to an advantageous embodiment of the invention the base body is configured as a carrier for at least one additional connection element, which is connected to the measuring channel through at least one connection spout.

According to an advantageous embodiment of the invention, at least one capillary is arranged in the at least one measuring channel. Advantageously the at least one capillary is configured a nozzle.

According to an advantageous embodiment of the invention the at least one capillary is configured as an insert, in particular a sealing wall of the at least one capillary is oriented in a direction of a mold extraction of an injection molded component. This way the part can be injection molded without requiring a slide. Alternatively, or additionally the at least one capillary can be connected through the at least one connection spout and the at least one connection element can be connected from an outside back again into the at least one measuring channel. Advantageously, intersection points can be arranged along a path of the measuring channels.

According to an advantageous embodiment of the invention, the at least one measuring channel includes at least one pump that is configured to generate a volume flow. The pump can be e.g. a membrane pump. Advantageously a sufficient volume flow can be implemented and damages through liquid substances in the gas can be avoided.

In particular the volume flow runs at least at 100 ml per minute, advantageously at least one standard liter per minute. The invention takes advantage of the fact that gases are being processed and that mass flows are much larger than in micro fluid applications.

According to an advantageous embodiment of the invention, a damping volume of at least 75 ml is arranged in the at least one measuring channel. Advantageously, this damping volume counteracts pumping pulses so that the pumping pulses can be dampened. Alternatively, or additionally a mass flow meter can be arranged in the at least one measuring channel.

According to an advantageous embodiment of the invention the at least one sensor unit includes a particle precipitator or impactor. Advantageously the impactor deflects an air flow so that heavy particles are precipitated and their mass or frequency can be analyzed.

According to an advantageous embodiment of the invention the at least one sensor unit includes an opto chemical sensor. This enables a detection of gaseous, e.g: toxic or combustible materials. Alternatively or additionally the at least one sensor unit can include an opto electronic sensor which may include the ability of scatter light measuring. This can enable a precise particle size analysis.

BRIEF DESCRIPTION OF THE DRAWINGS

The invention is subsequently described based on advantageous embodiments, but is not limited to these embodiments. Additional embodiments can be derived from combining features of individual or plural patent claims with one another or with individual or plural features of the embodiments. The advantageous embodiments are described with reference to drawing figures, wherein

DETAILED DESCRIPTION OF THE INVENTION

FIGS. 1-4 illustrates a gas measuring apparatus including core body in various embodiments.

Figure 1:
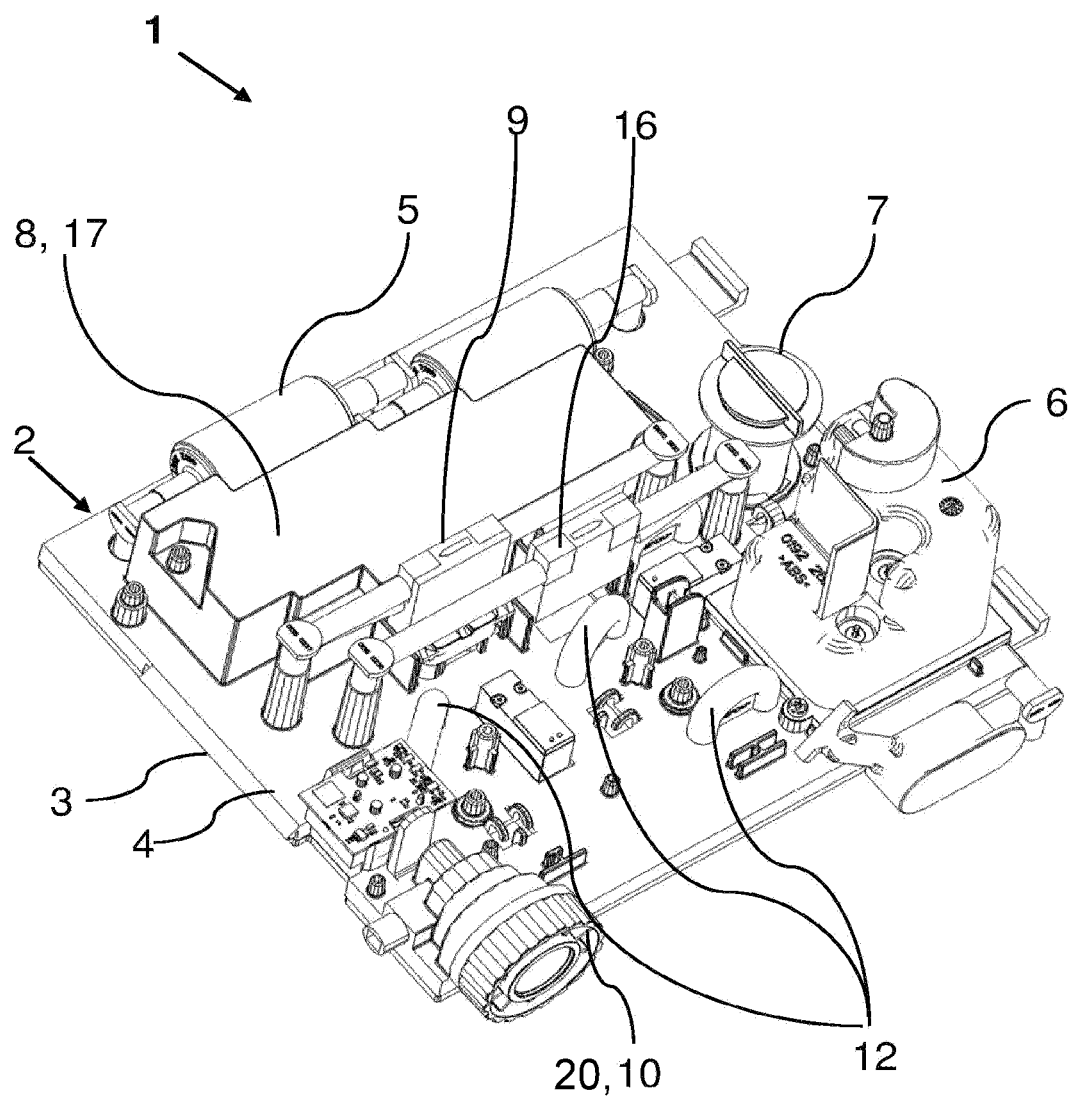
FIG. 1 illustrates a gas measuring apparatus including core body made from two parts in a perspective side view.

FIG. 1 shows the gas measuring apparatus 1 with the core body 2 in a perspective side view. It is evident from FIG. 1 that the gas measuring apparatus 1 includes the core body 2 including a first part 3 and a second part 4. The second part 4 of the core body 2 is configured as a cover.

The first part 3 and the second part 4 of the core body 2 are joined by atomic or molecular forces so that a bonded connection is created wherein the bonded partners can only be separated by destroying bonding devices.

Figure 2:
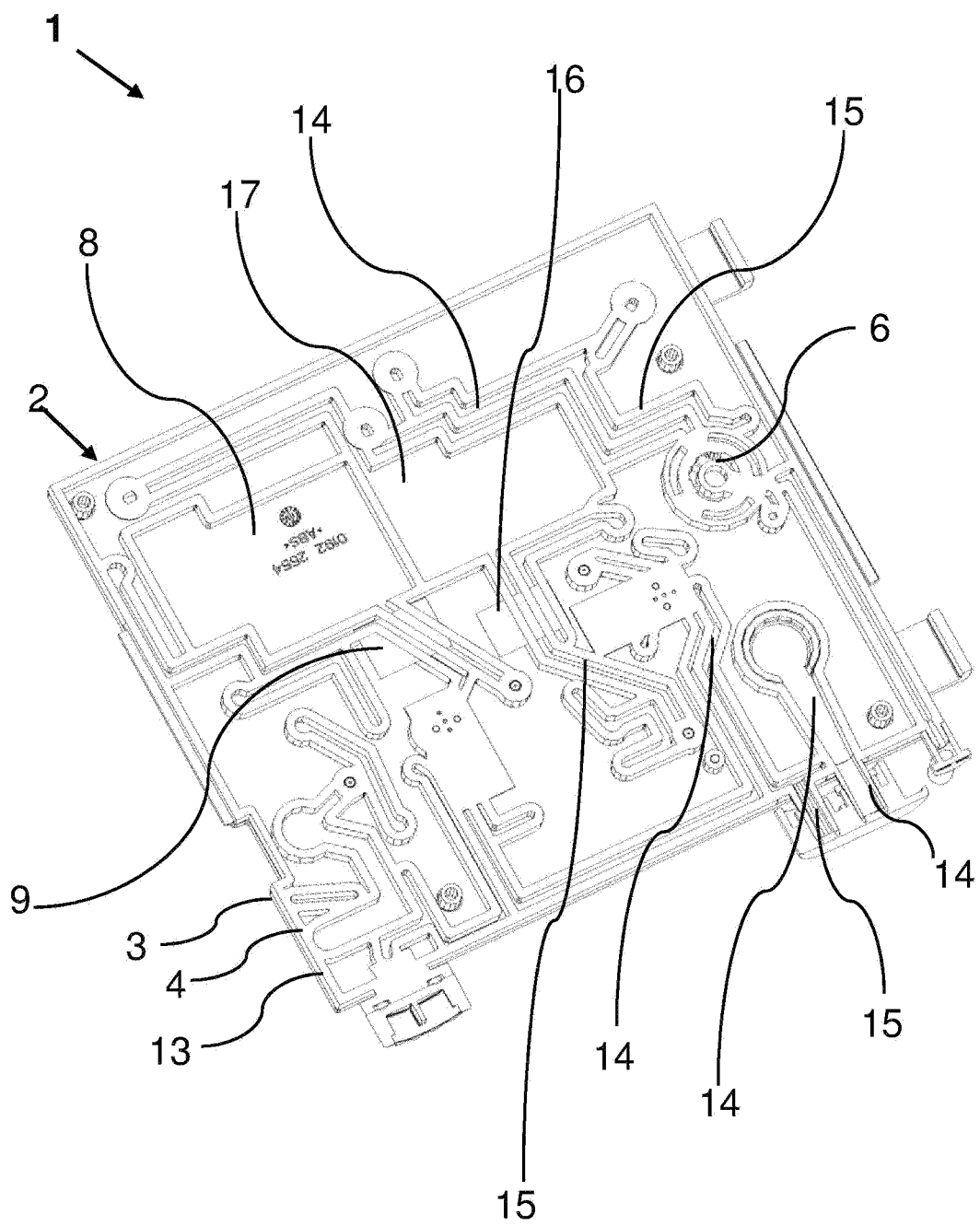
FIG. 2 illustrates the gas measuring apparatus with the core body made from two parts according to FIG. 1 in a cross-sectional view along an X-axis and a Z-axis showing a measuring channel.
Figure 3:
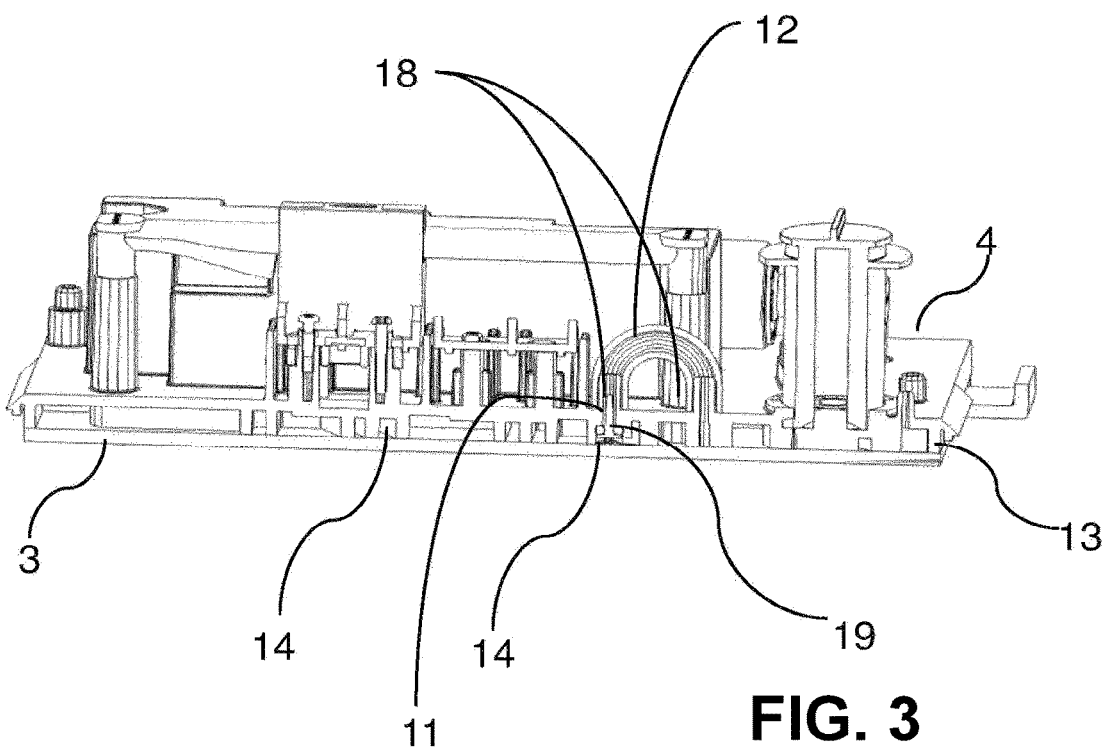
FIG. 3 illustrates the gas measuring apparatus including the core body made from two parts according to FIG. 1 in a cross-sectional view along a Y-axis and a Z-axis showing assembly of the first part and the second part at an interface in which a measuring channel is formed.
Figure 4:
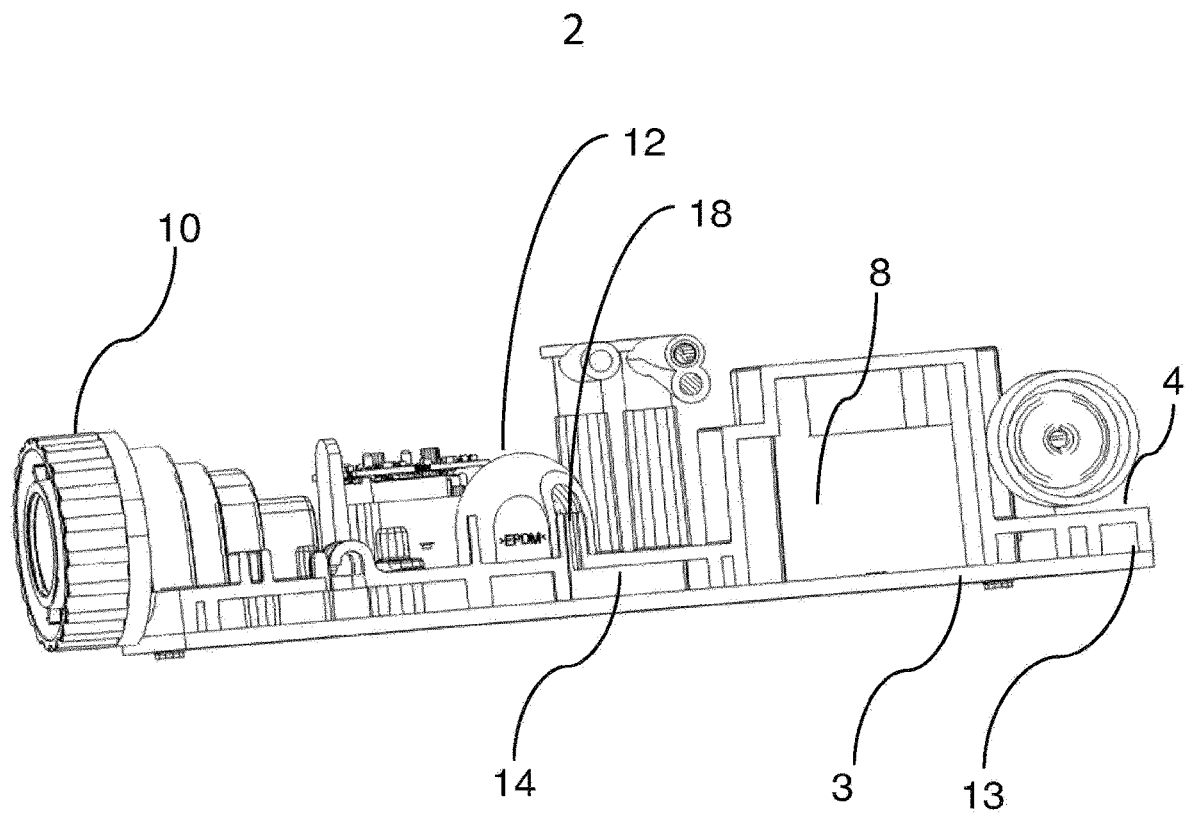
FIG. 4 illustrates the gas measuring apparatus with the core body made from two parts according to FIG. 1 in a cross-sectional view along the X-axis and the Y-axis showing a capillary arranged in the measuring channel.

FIGS. 1-4 illustrate that individual components of the gas measuring apparatus 1 are embedded in the core element 2 and enveloped by the core element 2. It is evident from the embodiments according to FIG. 1 and FIG. 2 that the component can be a filter 5, a pump 6, an additional pump 7, a damping volume 8, a mass flow measuring device 9 or a particle precipitator or impactor 10. Additional embodiments of the component of the gas measuring apparatus 1 can be a capillary 11 and a connecting element 12 as shown in FIGS. 3 and 4. It is furthermore evident from FIGS. 2-4 that the first part 3 is joined with the second part 4 at an advantageously flat and/or planar interface 13 in which a measuring channel 14 is formed. The gas to be measured to be conducted through the measuring channel 14 through a pump 6 and a mass flow measuring device 9 to the damping volume 8 as evident from FIG. 2. The pump 6 is formed to generate a volume flow. The damping volume 8 arranged in the core body 2 can counteract the pump pulses so that they are attenuated.

In order to dilute the gas to be measured and to adjust the gas to be measured to a sensitivity of the sensor at least one channel of a dilution flow 15 is formed in the base body in addition to the at least one measuring channel 14 as shown in FIG. 2. Accordingly, another pump, another mass flow measuring device and another damping volume 17 for the dilution gas are arranged in the base body 2.

FIGS. 1, 3 and 4 show that at least one connection element 12 is arranged in the base body wherein the at least one connection element 12 is connected by at least one connection spout 18 to the measuring channel 14. It is evident from the embodiment according to FIG. 1 that three connection elements 12 respectively including two connection spouts 18 are configured in the core body 2. Additional advantageous embodiments include a different number of connection elements 12, e.g. more than three connection elements or less than three connection elements and a different number of connecting spouts 18, e.g. more than two or less than two. Thus, the measuring channel 14 can be optionally connected to the respective connection elements through existing connection spouts as required for a particular installation space.

It is furthermore evident from FIG. 3 that the measuring channel 14 includes a capillary 11. The capillary 11 functions as a nozzle that regulates the measured flow. The capillary 11 and the measuring channel 14 are sealed gas tight relative to each other by a gasket 19. In order to be able to arrange intersection points along a path of the measuring channel the capillary 11 is connected through the connecting spout 18 and the connection element 12 from an outside back into the measuring channel 14 as illustrated in FIG. 3.

FIG. 1 also illustrates that a sensor unit 20 arranged in the measuring channel 14 includes a particle precipitator or impactor 10 configured to detect particles in the gas to be measured.

Thus, the invention provides a gas measuring apparatus 1 including at least one measuring channel 14 including at least one sensor unit 20 wherein the gas measuring apparatus 1 includes a core body 2 including a first part 3 and a second part 4 wherein the first part 3 is assembled at the second part 4 at a flat or planar interface 13 and the at least one measuring channel 14 is configured in the interface 13.

REFERENCE NUMERALS AND DESIGNATIONS 1 gas measuring apparatus
2 core body
3 first part of core body 2
4 second part of core body 2
5 filter
6 pump
7 additional pump
8 damping volume
9 mass flow measuring device
10 particle precipitator, impactor
11 capillary
12 connection element
13 interface
14 measuring channel
15 dilution flow channel
16 additional mass flow measuring device
17 additional dampening volume
18 connection spout
19 gasket
20 sensor unit

What is claimed is:

1. A gas measuring apparatus, comprising: at least one measuring channel including at least one sensor unit, a first pump configured to generate a volume flow in the measuring channel, a first mass flow measuring device, and a first damping volume; and a core body including a first part and a second part and a dilution flow channel, wherein the first part is joined at the second part at a flat or planar interface, and wherein the at least one measuring channel and the dilution flow channel are is configured in the flat or planar interface, wherein the dilution flow channel includes a second pump configured to generate a dilution flow in the dilution flow channel, a second mass flow measuring device, and a second damping volume, so that a gas to be measured is dilutable, and wherein the pump and the second pump are arranged at the first part of the core body.

2. The gas measuring apparatus according to claim 1,
wherein the second part of the core body is configured as a flat cover sheet, and
wherein the first part and the second part of the core body are bonded together.

3. The gas measuring apparatus according to claim 2,
wherein a bonded connection at the interface between the first part and the second part is formed by laser welding, and
wherein one of the first part and the second part is transparent and another of the first part and the second part is non-light permeable.

4. The gas measuring apparatus according to claim 1,
wherein the second part of core body supports plural additional U-shaped connection elements respectively arranged in at least two connection element planes oriented orthogonal to a plane of the flat or planar or planar interface and that are each connected through two respective connection spouts to the measuring channel, and
wherein the two respective connection spouts are integrally formed with the second part in one piece.

5. The gas measuring apparatus according to claim 4, wherein at least one capillary is arranged in the at least one measuring channel.

6. The gas measuring apparatus according to claim 5,
wherein the at least one capillary is configured as an injection molded insert,
wherein a sealing wall of the at least one capillary is oriented in a mold extraction direction of the injection molded insert, or
wherein the at least one capillary is connected through at least one connection spout and the at least one connection element from an outside back into the at least one measuring channel.

7. The gas measuring apparatus according to claim 1,
wherein the first pump is configured to generate a volume flow, and
wherein the volume flow is at least 100 ml per minute.

8. The gas measuring apparatus according to claim 1, wherein the at least one measuring channel includes a damping volume of at least 75 ml or a mass flow measuring device.

9. The gas measuring apparatus according to claim 1, wherein the at least one sensor unit includes a particle precipitator.

10. The gas measuring apparatus according to claim 1, wherein the at least one sensor unit includes an opto-chemical or an opto-electronic sensor.

* * * * *